(12) United States Patent
Griffey et al.

(10) Patent No.: US 6,253,168 B1
(45) Date of Patent: Jun. 26, 2001

(54) GENERATION OF VIRTUAL COMBINATORIAL LIBRARIES OF COMPOUNDS

(75) Inventors: Richard Griffey, Vista; Eric Swayze, Carlsbad, both of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/076,405

(22) Filed: May 12, 1998

(51) Int. Cl.⁷ .................. G06G 7/48; G06G 7/58
(52) U.S. Cl. .................. 703/12; 703/1; 703/5; 702/22; 702/27; 702/30; 702/32
(58) Field of Search .................. 395/500; 364/578; 435/6; 702/22, 27, 30, 32; 703/1, 2, 5, 12

(56) References Cited

U.S. PATENT DOCUMENTS

| | | | |
|---|---|---|---|
| 5,010,175 | 4/1991 | Rutter et al. | 530/334 |
| 5,186,898 | 2/1993 | Bridgham et al. | 422/102 |
| 5,372,672 | 12/1994 | Seifert et al. | 156/584 |
| 5,424,186 | 6/1995 | Fodor et al. | 435/6 |
| 5,434,796 | 7/1995 | Weininger | 364/496 |
| 5,472,672 | 12/1995 | Brennan | 422/131 |
| 5,529,756 | 6/1996 | Brennan | 422/131 |
| 5,565,324 * | 10/1996 | Still et al. | 435/6 |
| 5,573,905 * | 11/1996 | Lerner et la. | 435/6 |
| 5,574,656 | 11/1996 | Agrafiotis et al. | 364/500 |
| 5,703,792 | 12/1997 | Chapman | 364/496 |
| 5,880,972 * | 3/1999 | Horlbeck | 702/27 |

OTHER PUBLICATIONS

PCT International Search Report dated Jul. 7, 1999, 6 pages.
Czarnik et al (Editor), "A Practical Guide to Combinatorial Chemistry", American Chemical Society, ISBN 0–8412–3485–X, pp. 17–47 and 357–412, 1997.*

Levine et al, "Stalk: An Interactive System for Virtual Molecular Docking", IEEE Computational Science and Engineering, pp. 55–65, 1997.*

Waters et al, "Virtual Screening—An Overview", Drug Discovery Today, vol. 3 Issue 4, pp. 160–178, Apr. 1998.*

Chen et al., "Structure–Based Discovery of Ligands Targeted to the RNA Double Helix", *Biochem.*, 1997, 36, 11402–11407.

Chen et al., "Spectroscopic recognition of guanine dimeric hairpin quadruplexes by a carbocyanine dye", *Proc. Natl. Acad. Sci.*, 1996, 93, 2635–2639.

Gschwend et al., "Orientational sampling and rigid–body minimization in molecular docking revisited: On–the–fly optimization and degeneracy removal", *J. Compt.–Aided Mol. Des.*, 1996, 10, 123–132.

Kuntz et al., "A Geometric Approach to Macromolecule–Ligand Interactions", *J. Mol. Biol.*, 1982, 161, 269–288.

Kuntz et al., "Structure–Based Molecular Design", *Acc. Chem. Res.*, 1994, 27(5), 117–123.

(List continued on next page.)

*Primary Examiner*—Kevin J. Teska
*Assistant Examiner*—Samuel Broda
(74) *Attorney, Agent, or Firm*—Woodcock Washburn Kurtz Mackiewicz & Norris LLP

(57) ABSTRACT

The present invention provides methods for the generation of virtual libraries of compounds. These compounds are generated in silico. The present invention encompasses methods for tracking the addition of fragments, use of reagents, and transformations performed. Further, methods for interfacing the information necessary to generate libraries of compounds with instrumentation that conducts the actual synthesis of the compounds are provided. Also provided are methods for the in silico docking of the library compounds to identified target molecules of interest.

18 Claims, 20 Drawing Sheets

OTHER PUBLICATIONS

Meng et al., "Automated Docking with Grid–Based Energy Evaluation", *J. Comput. Chem.*, 1992, 13(4), 505–524.

Wilson, "Computers Customize Combinatorial Libraries: Computational methods can emphasize diversity or similarity, but the jury is still out on how well they work", *C& EN*, Apr. 17, 1998, 31–37.

Atherton, et al., in *Solid Peptide Synthesis: A practical Approach*, IRL Press, Oxford, UK, 1989, 135.

Brennan, T., et al., "Two–dimensional parallel array technology as a new approach to automated combinatorial solid–phase organic synthesis," *Augomation*, 1998, 33–45.

Corey, E.J. et al., "Computer–Assisted Analysis in Organic Synthesis," *Science*, 1985, 228, 408–418.

Czarnik, A. W. et al. (eds.), *A Practical Guide to Combinatorial Chemistry*, American Chemical Society, Washington, DC, 1997, Chs. 2, 13, and 14, 17–47 and 357–412.

Heathcock, et al., "Total synthesis of racemic vallesamidine," *J. Org. Chem.*, 1990, 55(3), 798–911 (abstract only).

Rotstein, S.H. et al., "GroupBuild: A Fragment–Based Method for De Novo Drug Design," *J. Med. Chem.*, 1993, 36, 1700–1710.

* cited by examiner

Compound CI
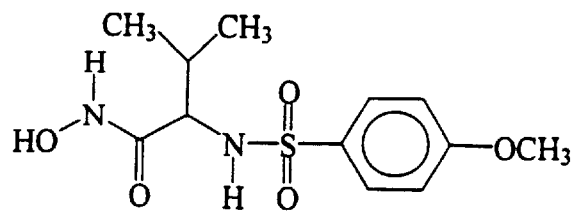
$C_{12}H_{18}N_2O_5S$
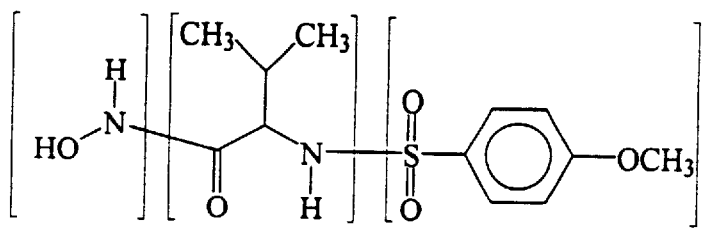
| | $F_i$ | $F_{ii}$ | $F_{iii}$ |
|---|---|---|---|
| Molecular formula | $H_2NO$ | $C_5H_9NO$ | $C_7H_7O_3S$ |
Figure 1

Addition of fragments to yield compounds
Table
| Fragment Identifier | Structure | Name | Molecular formula | Other |
|---|---|---|---|---|
| $F_i$ | 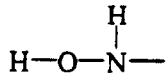 | Hydroxylamine | $H_2NO$ | ... |
| $F_{ii}$ | 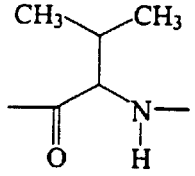 | Amino acid | $C_5H_9NO$ | ... |
| $F_{iii}$ | 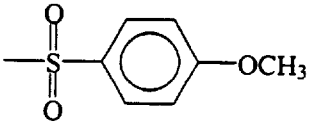 | Sulfonyl | $C_7H_7O_3S$ | ... |
Figure 2

| Reagents | Identifier | Name | Properties |
|---|---|---|---|
| H—O—NH₂ or ⓟ—O—NH₂ | R$_i$ | Hydroxylamine | ... |
| (FMOC blocked amino acid structure) | R$_{ii}$ | FMOC blocked amino acid | ... |
| (Sulfonylchloride structure) | R$_{iii}$ | Sulfonylchloride | ... |

ⓟ = Solid support

Figure 3

Common Fragment / Different Reagents and Transformations

Common Fragment / Different Reagents and Transformations

Common Reagent

Symbolic addition of fragments to yield compound

| Symbolic Structure | Symbolic Identifier | Molecular formula |
|---|---|---|

Fragment

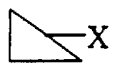  $F_{i'}$  $C_uH_vN_w ...$

  $F_{ii'}$  $C_uH_vN_w ...$

  $F_{iii'}$  $C_uH_vN_w ...$

Compound

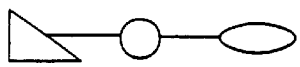  $CI'$  $C_uH_vN_w ...$ $$\begin{array}{r} \text{Molecular formula } F_{i'} \\ + \\ \text{Molecular formula } F_{ii'} \\ + \\ \underline{\text{Molecular formula } F_{iii'}} \\ = \text{Molecular formula } CI' \end{array}$$

Figure 7

Symbolic Reagent Table
| Identifier | Name | Structure | Molecular formula |
|---|---|---|---|
| R1 | xxx | 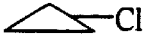 —Cl | xxx |
| R2 | ... | 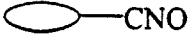 —CNO | ... |
| R3 | ... |  —Cl | ... |
| R4 | ... |  —Br | ... |
| R5 | ... | 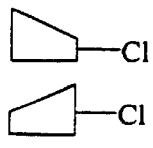 —Cl <br> 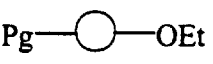 —Cl | ... |
| R6 | ... | Pg—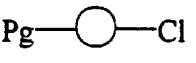—OEt | ... |
| R7 | ... | Pg—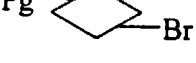—Cl | ... |
| R8 | ... | Pg—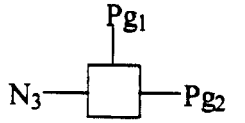—Br | ... |
| R9 | ... | $N_3$—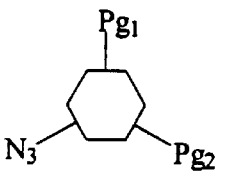—$Pg_2$ (with $Pg_1$ on top) | ... |
| R10 | ... | $N_3$—(hexagon with $Pg_1$ top and $Pg_2$)—$Pg_2$ | ... |
Figure 8

Symbolic Fragment Table

| Identifier | Symbolic Structure | Molecular formula | Molecular Weight |
|---|---|---|---|
| F1 | ▷—X | xxx | xxx |
| F2 | ⬭—X | ... | ... |
| F3 | ⬠—X | ... | ... |
| F4 | ▱—X / ▱—X | ... | ... |
| F5 | X—◯—Y | ... | ... |
| F6 | X—◇—Y | ... | ... |
| F7 | X—▢—Z with Y on top | ... | ... |
| F8 | X—⬡—Z with Y on top | ... | ... |

Figure 9

Symbolic Transformation Table
| Identifier | | Symbolic Reactions | | Reagent |
|---|---|---|---|---|
| T1 | F1 | 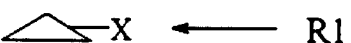—X ← R1 | | conditions α |
| T2 | F2 | —X ← R2 | | conditions β |
| T3 | F3 | 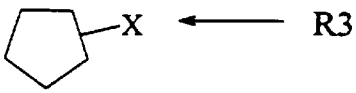—X ← R3 | | conditions α |
| T4 | F3 | 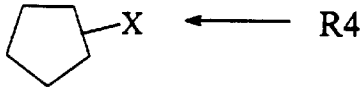—X ← R4 | | conditions α |
| T5 | F4 | 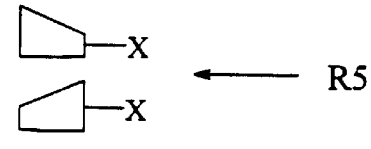 ← R5 | | conditions α |
| T6 | F5 | X—◯—Y ← R6 | | conditions ε |
| T7 | F5 | X—◯—Y ← R7 | | conditions α |
| T8 | F6 |  ← R8 | | conditions α |
| T9 | F7 |  ← R9 | | conditions γ |
| T10 | F8 |  ← R10 | | conditions γ |
Figure 10

Mixture 3

Mixture 4
2 Starting Fragments
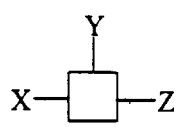
F7
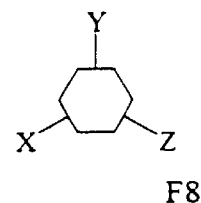
F8
2 Complex Fragments
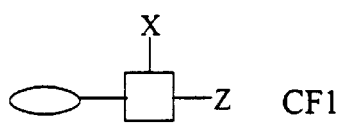 CF1
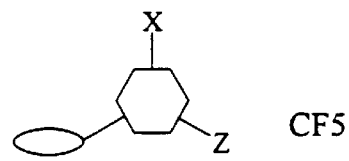 CF5
4 Complex Fragments
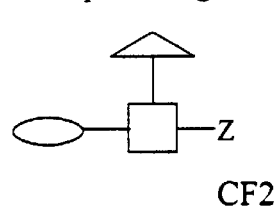
CF2
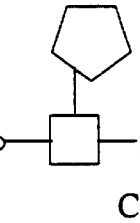
CF8
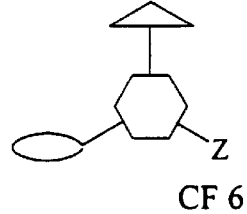
CF 6
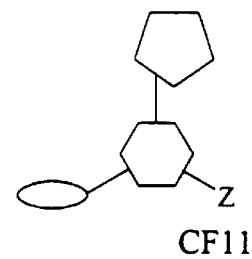
CF11
8 Complex Fragments
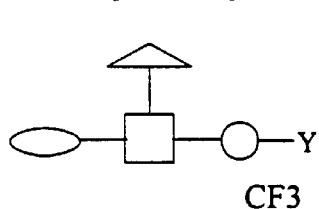
CF3
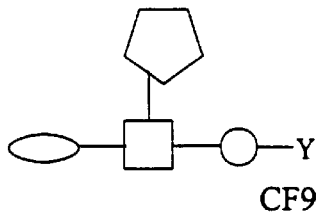
CF9
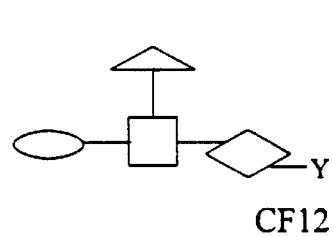
CF12
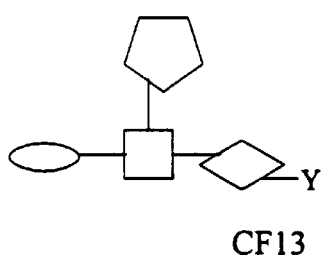
CF13
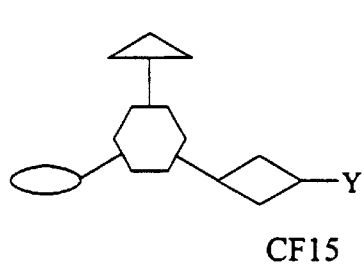
CF15
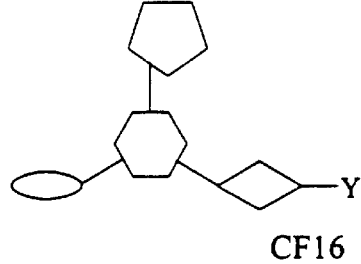
CF16
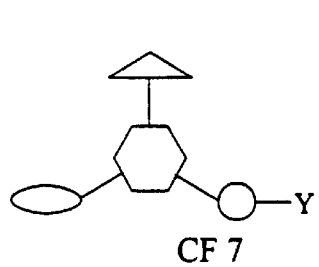
CF 7
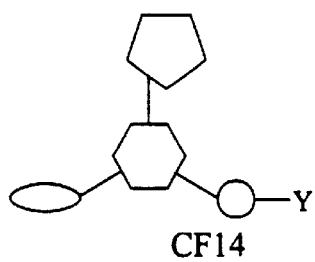
CF14
Figure 14a Mixture 4 (continued)

16 compounds

Tracking Table for Compound C1

(a) By Fragments:

| n | n+1 | n+2 |
|---|-----|-----|
| F7 | | |
| | F2 | |
| | F1 | |
| | F5 | |
| | | F3 |

(b) By Transformations:

Synthesis Path 1

| n | n+1 | n+2 |
|---|-----|-----|
| T9 | | |
| | T2 | |
| | T1 | |
| | T6 | |
| | | T3 |

Synthesis Path 2

| n | n+1 | n+2 |
|---|-----|-----|
| T9 | | |
| | T2 | |
| | T1 | |
| | T7 | |
| | | T3 |

Synthesis Path 3

| n | n+1 | n+2 |
|---|-----|-----|
| T9 | | |
| | T2 | |
| | T1 | |
| | T6 | |
| | | T4 |

Synthesis Path 4

| n | n+1 | n+2 |
|---|-----|-----|
| T9 | | |
| | T2 | |
| | T1 | |
| | T7 | |
| | | T4 |

Figure 15

Tracking Table

Tracking M1

Step 1
| T9 |   |

Step 2
| T9 | T2 |

Step 3
| T9 | T2<br>T1 |

Step 4
| T9 | T2<br>T1<br>T7 |

Step 5
| T9 | T2<br>T1<br>T7 | $T5^1$ |

C2

Step 5
| T9 | T2<br>T1<br>T7 | $T5^2$ |

Tracking Table

Tracking M2

Step 1

| n | n+1 | n+2 |
|---|---|---|
| T9 | | |

Step 1

| n | n+1 | n+2 |
|---|---|---|
| T10 | | |

Step 2

| n | n+1 | n+2 |
|---|---|---|
| T9 | T2 | |

Step 2

| n | n+1 | n+2 |
|---|---|---|
| T10 | T2 | |

Step 3

| n | n+1 | n+2 |
|---|---|---|
| T9 | T2 | |
| | T1 | |

Step 3

| n | n+1 | n+2 |
|---|---|---|
| T10 | T2 | |
| | T1 | |

Step 4

| n | n+1 | n+2 |
|---|---|---|
| T9 | T2 | |
| | T1 | |
| | T7 | |

Step 4

| n | n+1 | n+2 |
|---|---|---|
| T10 | T2 | |
| | T1 | |
| | T7 | |

Step 5

| n | n+1 | n+2 |
|---|---|---|
| T9 | T2 | |
| | T1 | |
| | T7 | |
| | | T4 |

Step 5

| n | n+1 | n+2 |
|---|---|---|
| T10 | T2 | |
| | T1 | |
| | T7 | |
| | | T4 |

Tracking Table
Tracking M3
Step 1
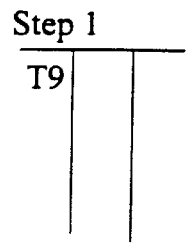
Step 2
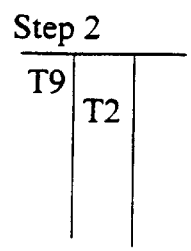
Step 3
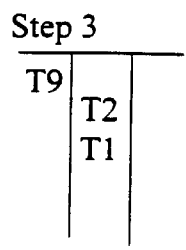
Step 3
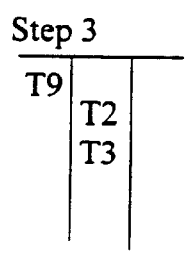
Step 4
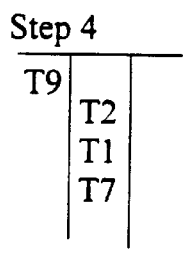
Step 4
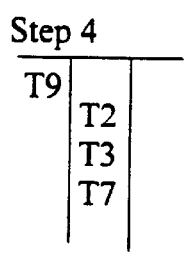
Step 5
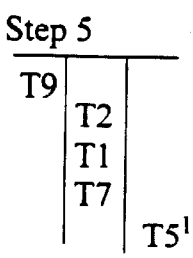
C2
Step 5
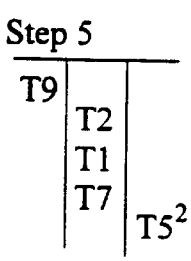
C3
Step 5
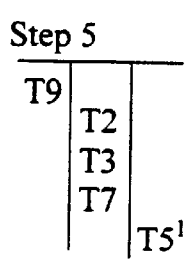
C7
Step 5
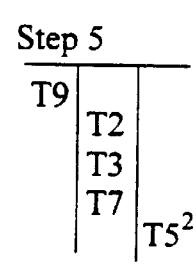
C8
Figure 18

GENERATION OF VIRTUAL COMBINATORIAL LIBRARIES OF COMPOUNDS

FIELD OF THE INVENTION

The present invention is directed to methods for the generation of virtual combinatorial libraries of small molecules and other ligands. The members or molecules of the combinatorial libraries are generated in silico, and are designed to bind to identified target molecules in silico. The present invention also includes methods for docking the library members to desired target molecules whereby the library members are bound to such targets in silico.

BACKGROUND OF THE INVENTION

Combinatorial chemistry is a recent addition to the toolbox of chemists and represents a field of chemistry dealing with the synthesis of a large number of chemical entities. This is generally achieved by condensing a small number of reagents together in all combinations defined by a given reaction sequence. Advances in this area of chemistry include the use of chemical software tools and advanced computer hardware which has made it possible to consider possibilities for synthesis in orders of magnitude greater than the actual synthesis of the library compounds. The concept of "virtual library" is used to indicate a collection of candidate structures that would theoretically result from a combinatorial synthesis involving reactions of interest and reagents to effect those reactions. It is from this virtual library that compounds are selected to be actually synthesized.

Project Library (MDL Information Systems, Inc., San Leandro, Calif.) is said to be a desktop software system which supports combinatorial research efforts. (*Practical Guide to Combinatorial Chemistry,* A. W. Czaniik and S. H. DeWitt, eds., 1997, ACS, Washington, D.C.) The software is said to include an information-management module for the representation and search of building blocks, individual molecules, complete combinatorial libraries, and mixtures of molecules, and other modules for computational support for tracking mixture and discrete-compound libraries.

Molecular Diversity Manager (Tripos, Inc., St. Louis, Mo.) is said to be a suite of software modules for the creation, selection, and management of compound libraries. (*Practical Guide to Combinatorial Chemistry,* A. W. Czarnik and S. H. DeWitt, eds., 1997, ACS, Washington, D.C.) The LEGION and SELECTOR modules are said to be useful in creating libraries and characterizing molecules in terms of both 2-dimensional and 3-dimensional structural fingerprints, substituent parameters, topological indices, and physicochemical parameters.

Afferent Systems (San Francisco, Calif.) is said to offer combinatorial library software that creates virtual molecules for a database. It is said to do this by virtually reacting precursor molecules and selecting those that could be actually synthesized (Wilson, *C&EN,* Apr. 27, 1998, p.32).

While only Project Library and Molecular Diversity Manager are available commercially, these products do not provide facilities to efficiently track reagents and synthesis conditions employed for the introduction of fragments into the desired compounds being generated. Further, these products are unable to track mixtures of compounds that are generated by the introduction of multiple fragments by the use of multiple reagents. Therefore, it is desirable to have available methods for handling mixtures of compounds, as well as methods for the tracking of chemical reactions or transformations utilized in the synthesis of individual compounds and mixtures thereof.

SUMMARY OF THE INVENTION

In accordance with the present invention, there are provided methods for the generation of virtual combinatorial libraries of small molecules. These library molecules or members are generated in silico. Library members of larger molecular weight, such as those that are polymeric in nature, may also be generated using the methods of the present invention.

The present invention further provides methods for tracking and maintaining in databases, the fragments, reagents and unique combinations of these used for the in silico generation of the library members. Methods for interfacing the information necessary for the generation of libraries in silicon as instructions designed to direct the actual synthesis of the library members on an instrument such as a parallel array synthesizer, are also provided in the present invention.

The present invention also provides methods for the in silico docking of the library members to identified target molecules. According to these methods, individual library members are allowed to bind to the desired target molecule in order to identify those library members that demonstrate high affinity binding to the targets.

While there are a number of ways to identify molecular interaction sites, identify compounds likely to interact with molecular interaction sites of RNA and other biological molecules, synthesize such compounds and analyze their binding, preferred methodologies are described in U.S. patent applications filed on even date herewith and assigned to the assignee of this invention. These application bear U.S. Ser. Nos. 09/076,440, 09/076,447, 09/076,206, 09/076,214 and 09/076,404, each of which was filed May 12, 1998. All of the foregoing applications are incorporated by reference herein in their entirety.

BRIEF DESCRIPTION OF THE DRAWINGS

FIG. 1 shows a compound CI, dissected into its constituent fragments;

FIG. 2 shows the various identifying characteristics of the fragments comprising compound CI;

FIG. 3 shows the various identifying characteristics of the reagents used to introduce the corresponding fragments comprising compound CI;

FIG. 7 shows the symbolic addition of fragments yielding a symbolic compound, compound CI';

FIG. 8 is a symbolic reagent table;

FIG. 9 is a symbolic fragment table;

FIG. 10 is a symbolic transformation table;

FIGS. 14a and 14b show the generation of an additional mixture, mixture M4;

FIG. 15 shows tables for tracking compound C1 by the fragments added and or transformations performed;

FIG. 16 shows tables for tracking mixture M1 by the transformations performed;

FIG. 17 shows tables for tracking mixture M2 by the transformations performed; and FIG. 18 shows tables for tracking mixture M3 by the transformations performed.

Figure 4:
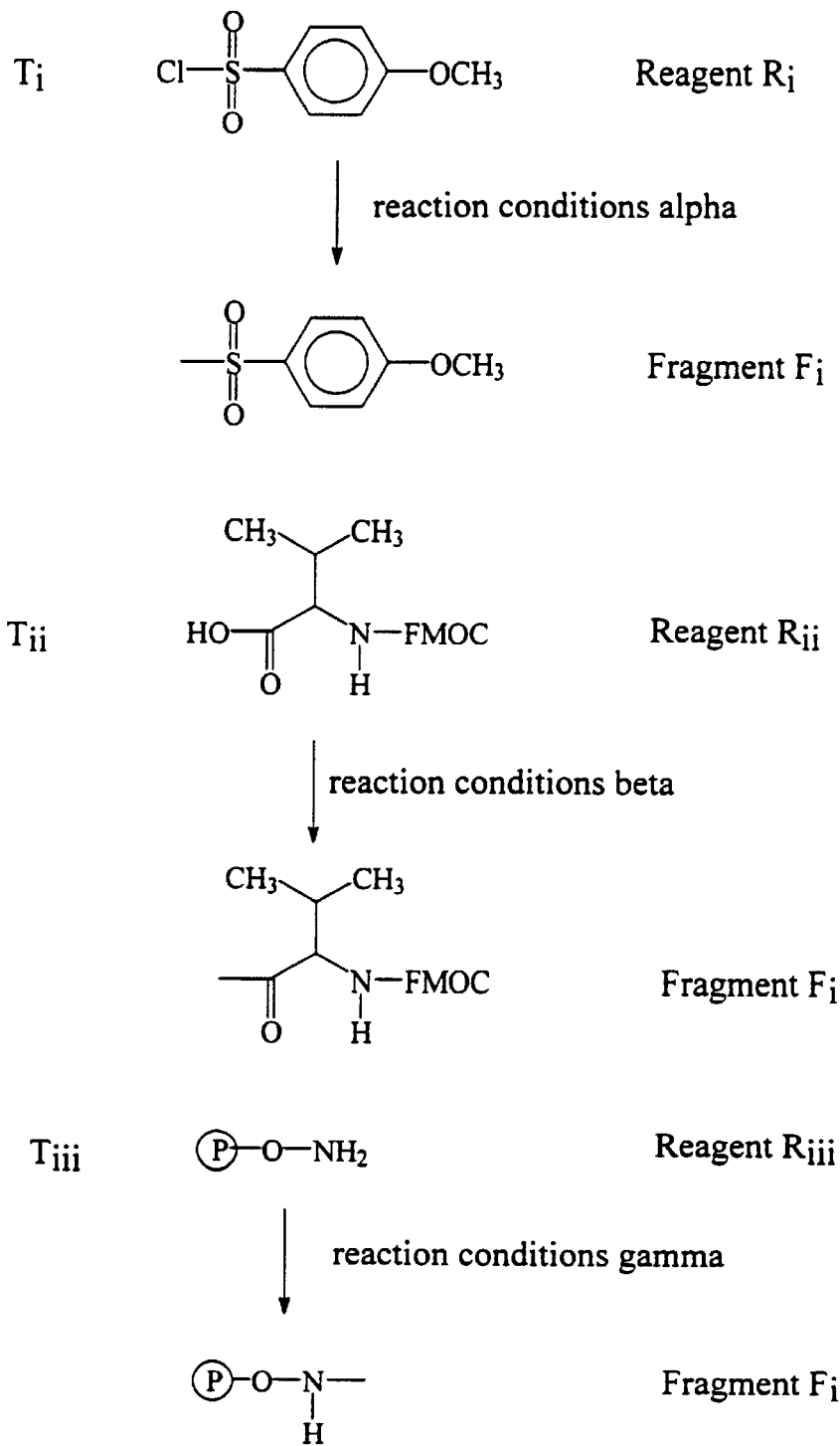
FIG. 4 is a list of transformations that link the fragments and reagents associated with the generation of compound CI.

The present invention is directed to computational methods employed for the in silico design and synthesis of combinatorial libraries of small molecules. The library members are generated in silico. The present invention also encompasses methods for tracking and storing the information generated during the in silico creation of library members into relational databases for later access and use. For the purposes of this specification, in silico refers to the creation in a computer memory, i.e., on a silicon or other like chip. Stated otherwise in silico means "virtual."

According to the methods of the present invention, each compound or library member is dissected into its component or constituent parts referred to as fragments. Thus each compound that is generated is considered to be comprised of constituent fragments such that the sum of the molecular formulas of each of the fragments when added together totals the molecular formula of the compound generated. This dissection can be done in a variety of ways using chemical intuition. Thus a variety of components of fragments may be identified, each of which lend themselves to readily available reagents or reactions to generate diverse compounds. Further, each fragment is associated with at least one reagent, which represents the necessary chemical to be used to introduce that desired fragment into the compound being generated in silico. Dissection of compounds is based on the ease of synthesis of the reagents, commercial availability of the reagents, or a combination of both. Each of the fragments and reagents are stored in a relational database and are described in terms of identifying characteristics in the database. A fragment may be available from a variety of starting materials or reaction schemes. So when a library is being generated, which entails building a database, the fragments used in building that library can be stored in the database using the corresponding set of reagents and reaction conditions. When another library is to be generated, the fragment information stored in the database is now available for use in the generation of the new library of compounds. Similarly, when a third library is being generated, an even greater quantity of fragment, reagent, and reaction information is available in the database. Thus the methods of the present invention represent a dynamic method of building a database associated with building libraries of compounds. Initial library generation requires database input for fragments, reagents and transformations necessary for desired library. As the database grows, however, an increasing number of fragments and reagents are available in the database, which simplifies the generation of subsequent libraries of compounds and makes for more routine combinatorial synthetic efforts which can be accomplished with increasing ease and efficacy.

Fragments that are recorded in the database may be defined using identifying characteristics. Identifying characteristics defining fragments include a structural representation (as a 2-dimensional or 3-dimensional file), name, molecular weight, molecular formula, and attachment points or nodes (which denote sites of attachment or linkage of the fragment to other fragments of the compound being generated in silico). For the purpose of describing this invention, 2-dimensional representations are used, which are further simplified by the use of symbolic representations without reference to any particular chemical entities. The symbolic representations as used herein merely shows how fragments can be tracked to further the methods of the present invention. Other identifying characteristics may also be added to the database. Any characteristic that is desired to be tracked may be included in the database, including biological data, chemical reactivity rates, or other physical or chemical properties. Further, a fragment may also be created by modifying a reagent, and such modifications can be added to the database in terms of changes made to the reagent structure. Some of the identifying characteristics associated with any fragment may be common to those of the corresponding reagent. The related fragment thus created can then be stored in the relational database.

Identifying characteristics defining reagents include a structural representation, name, molecular weight, molecular formula, and source, such as a commercial source or a unique compound defined by the user. In case of a commercial source for the reagent, a catalog number or a link to a web page can be provided. Some commonalities may exist between the identifying characteristics associated with a reagent and those associated with the related fragment.

Further, in accordance with the present invention, a compound is the sum of various transformations. Transformation is the nomenclature attributed according to the present invention to a chemical synthesis. A transformation is a 1:1 link between a fragment and a reagent. Thus each transformation describes a unique conversion of a reagent into the corresponding fragment as introduced into a compound. When the compound being generated in silico is broken down into its component fragments, and the corresponding reagents have been identified, each fragment is linked to the corresponding reagent in a 1:1 relationship in order to describe a transformation. Thus, according to the present invention, a transformation may be viewed as the source of a fragment, thereby linking that fragment to a particular synthetic method or reaction. This description of a transformation according to the methods of the present invention also includes any auxiliary reagents or conditions used to effect the reaction denoted by the transformation, such as temperature and pressure requirements, catalysts, activators, solvents, or other additives.

Each combination of a fragment and reagent in a 1:1 link comprises a different transformation. Therefore, each transformation is unique. The present invention allows the tracking of fragments in terms of the reaction or transformation in which those fragments are introduced into the compounds of the library. Thus the database describes not only the compounds generated in terms of their constituent fragments, but also in terms of the synthetic pathways to produce those compounds, i.e. the related transformations to generate the library compounds. In this manner, a user of the present invention can generate a virtual library of compounds by simply selecting the fragments desired. Alternately, a user can also generate the compounds by selecting the chemical pathways required for actual synthesis of the compounds. This is accomplished by selecting the appropriate transformation associated with the generation of the desired compounds. Here, the user uses intuition or an in silico expert system to assist in selecting those transformations that are expected to allow generation or synthesis of the desired compounds. Each of the transformations created in silico is stored in the relational database and described in terms of identifying characteristics. Identifying characteristics defining transformations include the fragment, the reagent, and any auxiliary reagent or conditions necessary to effect the conversion of the reagent into the fragment as incorporated into the compound.

For example, consider in FIG. 1 the in silico generation of compound CI according to the methods of the present invention. As shown in FIG. 1, upon dissection of CI (molecular formula of $C_{12}H_{18}N_2O_5S_1$), its constituent fragments can be denoted as $F_1$ (molecular formula of $H_2NO$), $F_{ii}$ (molecular formula of $C_5H_9NO$), and $F_{iii}$ (molecular formula of $C_7H_7O_3S$). $F_i$ can also be a hydroxyl amine moiety linked to a solid support, i.e. P-O-NH, wherein P is a solid support. The sum of the molecular formulas of each of the fragments totals the molecular formula of compound CI.

As shown in FIG. 2, each of the fragments, $F_i$, $F_{ii}$, and $F_{iii}$, are stored in a relational database, and are described in terms of identifying characteristics including a structural representation (which may be 2-dimensional or 3-dimensional), an identifier or name, molecular formula and attachment points or nodes which signify sites on the fragment which are linked to other fragments in compound CI. Other information such as molecular weight can also be associated with the fragment in the database.

As shown in FIG. 3, each of the corresponding reagents ($R_i$, $R_{ii}$, and $R_{iii}$) are also stored in the relational database, and described in terms of identifying characteristics. Identifying characteristics used to define the reagents include a structural representation, and identifier or name and molecular formula. As with the fragment, other associated information such as molecular weight and source (such as a commercial source verses user-supplied, amount on hand, special handling, etc.) can also be stored in database in association with the individual reagents.

Next, each of the transformations associated with the in silico generation of compound CI are also stored in the relational database. As shown in FIG. 4, transformation $T_i$ links reagent $R_i$ with fragment $F_i$, $T_{ii}$ links $R_{ii}$ with $F_{ii}$, and $T_{iii}$ links $R_{iii}$ with $F_{iii}$ in a 1:1 relationship. Also, associated with each transformation is the necessary reaction condition, so that transformation $T_i$ is associated with reaction condition alpha, $T_{ii}$ with reaction condition beta, and $T_{iii}$ with reaction condition gamma. In the case of transformation $T_{iii}$, reagent $R_{iii}$ may be a hydroxyl amine attached to a solid support so that fragment $F_{iii}$ can be represented as a hydroxyl amine moiety attached to a solid support.

Figure 5:
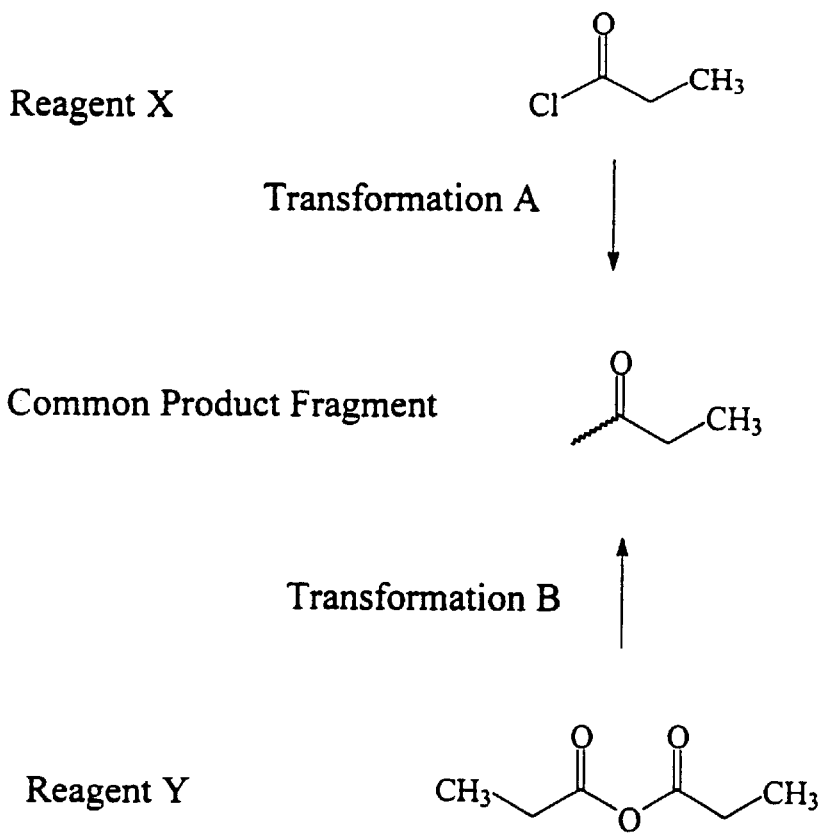
FIG. 5 is a schematic for the introduction of a common fragment using two different reagents.

While each fragment may be arrived at or generated by a unique corresponding reagent, the present invention also encompasses common fragments that may be generated via two or more reagents, so that two or more transformations can lead to the same fragment. As shown in FIG. 5, the common fragment $CH_3-CH_2-C(=O)-$ may be arrived at via transformation A, which employs reagent X (an acid chloride), $CH_3-CH_2-C(=O)Cl$. The common fragment can also be introduced into a compound being generated in silico via transformation B, which employs reagent Y (an acid anhydride), $CH_3-CH_2-C(=O)-O-C(=O)-CH_2-CH_3$. Therefore, in accordance with the methods of the present invention, a common fragment can be introduced into the compound via two or more different reagents, and thus via two or more distinct transformations.

Figure 6A:
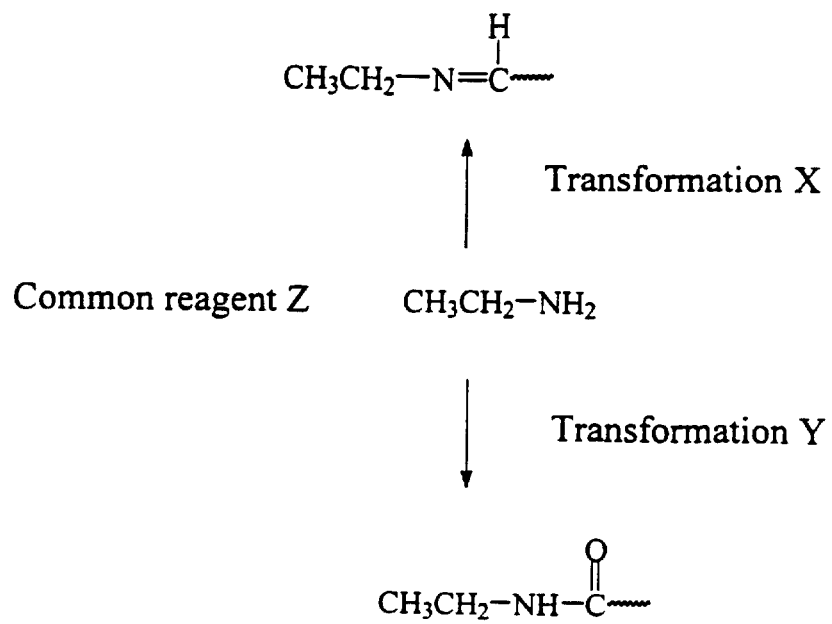
FIG. 6a is a schematic for the use of a single reagent for the introduction of two different fragments into a compound.

Alternately, a common reagent may be employed to effect two or more conversions forming two or more different fragments. This then represents two or more different transformations associated with different conditions. For example, as shown in FIG. 6a, common reagent Z, $CH_3-CH_2-NH_2$, can be employed to introduce an alkene fragment into the compound under conditions favoring Schiffs base formation. This represents transformation X. The same common reagent Z, however, can also be employed to introduce an amide fragment into the compound by using a different set of conditions, constituting transformation Y. Thus, a common reagent can introduce two or more different fragments into final compounds being generated in silico, and can be associated with two or more transformations depending upon the conditions associated with each of those transformations.

Figure 6B:
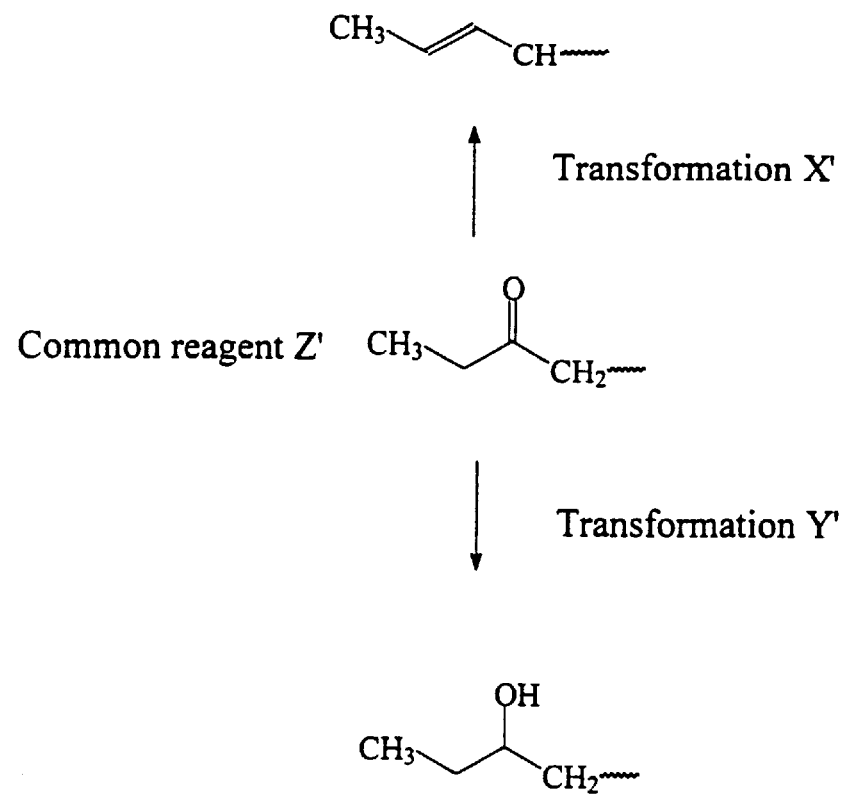
FIG. 6b is a schematic showing the use of a common reagent for the introduction of a common fragment compound which can further be converted into two different fragments within the compound generated.

Additionally, once a fragment has been introduced into a compound, it can be further modified and converted into yet another fragment without effecting any other chemical changes within the compound formed. As an example, shown in FIG. 6b, consider common reagent Z', $CH_3-CH_2-C(=O)CH_2-Cl$. Common reagent Z' corresponds to a fragment having the structure $CH_3-CH_2-C(=O)CH_2-$. Common reagent Z' may be used to introduce an alkene fragment into the final compound, representing transformation X', under conditions favoring reduction and dehydration. Common reagent Z', however, can also be used to introduce a hydroxyalkyl fragment into the final compound under conditions favoring reduction. This represents transformation Y'.

The present invention may be described more generally, in terms of symbolic representations. Symbolic representations are used to describe the methods of the present invention because such representations are not limited to any particular chemistry. Symbolic representations merely denote the manner of using the present invention with multiple chemical entities. Each symbol used in the representations describing the present invention may represent one compound or multiple compounds because the present invention is not limited to tracking a single compound, but may be used to track a vast variety of compounds that can be generated.

FIG. 7 shows the symbolic addition of fragments which yields compound CI'. The fragments have structures $F_i$, $F_{ii}$, and $F_{iii}$ that are added sequentially to yield compound CI'. Structures $F_i$, $F_{ii}$, and $F_{iii}$ are symbolic representations of the fragments that constitute compound CI'. These fragments can be stored in the relational database with the corresponding identifying characteristics for each of them, including the structural representation, name, molecular formula, and attachment sites or nodes. A visual inspection of compounds C1 and C1' revels the commonality between the chemical compound C1 and the symbolic representation of a compound C1' as well as the chemical structure of the fragments and the symbolic structure of the fragments.

A symbolic reagent table is shown in FIG. 8. Reagents R1 to R10 can be described in terms of their structure, name, molecular formula, molecular weight, and source as well as other information that might be desired to be associated with the reagents.. R3 and R4 are two different reagents, but may be used to introduce the same fragment into a compound. This depends upon the reaction conditions used as reagent R3 is used in a transformation associated with one set of conditions, while reagent R4 is used in another transformation associated with a different set of conditions. Also, reagent R5 is comprised of a mixture of two reagents or components. These may be (R)- and (S)-stereoisomers, D- and L-isomers, or may be two completely different reagents. While R5 here is represented as a mixture of only two reagents or components, it will be recognized by the art-skilled that the methods of the present invention may be practiced using a mixture of two or more reagents. Typical reagent mixtures used in constructing libraries might have four, five or more individual reagent constituting the mixture.

FIG. 9 shows a symbolic fragment table. Fragments F1 to F8 are stored in the relational database with identifying characteristics that include a structural representation, name, molecular weight, molecular formula, and attachment sites or nodes. This table depicts symbolic representations of the various fragments that are introduced into the compounds of the library by the use of reagents symbolized in FIG. 8. Thus it can be seen that fragment F1 can be introduced into the compound by employing reagent R1. In fragment F1, X is an identifier for an attachment site. This indicates that X is the site at which F1 attaches to another fragment in a compound. Similarly, fragment F2 may be introduced into a compound (attaching at its X site) by employing reagent R2.

Fragment F3, however, can be introduced into the compound by the use of either reagent R3 or R4. This allows for selection in the choice of the reagent used, and also allows for the consideration of the compatibility of the chemistries involved in the introduction of other fragments into the compound. Next, fragment F4 (which is a mixture of fragments) can be introduced via the use of reagent R5, which is a mixture of reagents, as shown in FIG. 8.

Fragment F5 has two attachment sites, indicating that other fragments can attach at sites X and Y when F5 has been incorporated into a compound. The presence of two attachment sites indicates that two attachments may be undertaken to build a compound when dealing with F5. Here again, as before, F5 can be introduced into the compound using either of reagents R6 or R7, depending upon the reaction conditions used and the chemistries involved when introducing other fragments to build the compound.

Fragments F7 and F8 can be introduced into a compound being created in silico by employing reagents R9 and R10, respectively. Both these fragments have three attachment sites, indicating that three attachments to other fragments can occur when using these fragments to build a compound in silico. While fragments F7 and F8 have three attachment sites, it is recognized by the art-skilled that more than three attachment sites may be present in a fragment, allowing for more attachments to the fragment upon introduction into a compound (with the use of an appropriate reagent).

With the fragment and reagent tables in place in the relational database, a transformation table is created in accordance with the methods of the present invention, by linking a fragment with a reagent to form a unique transformation. FIG. 10 shows a symbolic transformation table where a fragment is linked to a reagent in a 1:1 relationship. The identifying characteristics describing each transformation include a 1:1 link (a one to one link) between a fragment and a reagent, and the reaction conditions which include, solvent, concentration, temperature and pressure requirements, or auxiliary reagents necessary to effect the introduction of the fragment into the compound by using an appropriate reagent. Auxiliary reagents include catalysts, activators, acids, bases or other chemicals or additives necessary to effect the fragment introduction described. For example a base can always be added with an alkyl halide to scavenge the acid generated with use of the alkyl halide.

As seen in FIG. 10, transformation T1 links fragment F1 with reagent R1. T1 also specifies the reaction conditions (a) associated with this 1:1 link. Similarly, T2 links F2 with R2 under conditions $\beta$. Transformations T3 and T4 are each unique transformations despite being associated with a common fragment, F3. Transformation T3 links common fragment F3 with reagent R3 under conditions $\alpha$, while transformation T4 links the common fragment F3 with another reagent, R4, under the different conditions, conditions $\delta$. For example reagent R3 might be an alkyl chloride while R4 might be an alkyl iodide. While these reagents are similar (they are both alkyl halides), they might be used under different reaction conditions. Use of different reagents to effect the introduction of the same fragment into the compound being generated in silico represents two unique transformations. This indicates two distinct or unique synthetic ways of introducing the same fragment into the compound. Depending upon the totality of the chemical steps involved in synthesizing the compound, one transformation may be preferred over other transformations that introduce the same fragment into the compound.

Transformation T5 links fragment F4 with reagent R5. R5 is a mixture of reagents, such as (R)- and (S)-stereoisomers, D- and L-isomers, or two or more different reagents. As a result, use of R5 leads to the introduction of a mixture of fragments F4 into the compound. The art-skilled will recognize that the multiple reagents in R5 are selected such that they are capable of being mixed together, do not react with each other, and react under similar reaction conditions. For example, R5 may be comprised of a mixture of acid halides. These do not react with each other, but do react similarly with a nucleophile under similar conditions. It is also recognized by the art-skilled that a reagent is not limited to only one or two components or constituent reagents, but in fact may comprise of two, three, four, five or more reagents or components.

When using a mixture of reagents, each of the individual component reagents may have different chemical reactivity rates. If a correction is not made for this, this could result in their products being unequally represented in the product compounds. This is solved by adjusting the concentration of each reagent in the reaction mixture relative to the other reagents in the mixture such that the relative rates are the same. This is effected by comparing to the reactivity of each of the reagents to a chosen standard reagent. The standardized reactivity rates can then be used to adjust the concentration of each constituent reagent in the reagent mixture to compensate for the varied reaction rates. Thus a mixture of reagents with different reaction rates may be used in one reagent mixture to still generate equivalent quantities of the desired compounds in the library.

Transformations T6 and T7 are similar to transformations T3 and T4 except that conditions identifying each of these transformations are different. Transformation T6 links fragment F5 with reagent R6 under conditions $\epsilon$, while transformation T7 links the same fragment F5 with a different reagent R7 under different conditions (condition $\alpha$). As the conditions associated with transformations T6 and T7 are different, this allows selection of compatible chemistries with other fragments during any particular synthesis being used. This is a very useful and very important consideration in actually synthesizing real libraries. When it is desired to introduce fragment F5 into the compound, the actual chemistries used to build the compound can be initially be considered in selecting transformation T6 or T7, and thus reagents R6 or R7. This is in direct opposition to any chemical database generator that only considers the compound structure not the actual chemistries necessary to build a compound.

Transformations T9 and T10 link fragment F7 with reagent R9 and fragment F8 with reagent R10, respectively.

Both transformations are identified to be associated with reaction conditions γ. Fragments F7 and F8 have three attachment sites, but it is recognized that these fragments may have more than three attachment sites, thereby increasing the complexity of the compounds generated, and increasing the number of rounds that may be employed to attach other fragments. For the three sites illustrated, if three sets of different reagent mixtures each have five reagents in the set are used, then 125 compounds will be generated for fragment F7 and a further 125 compounds will be generated for fragment F8.

Figure 11:
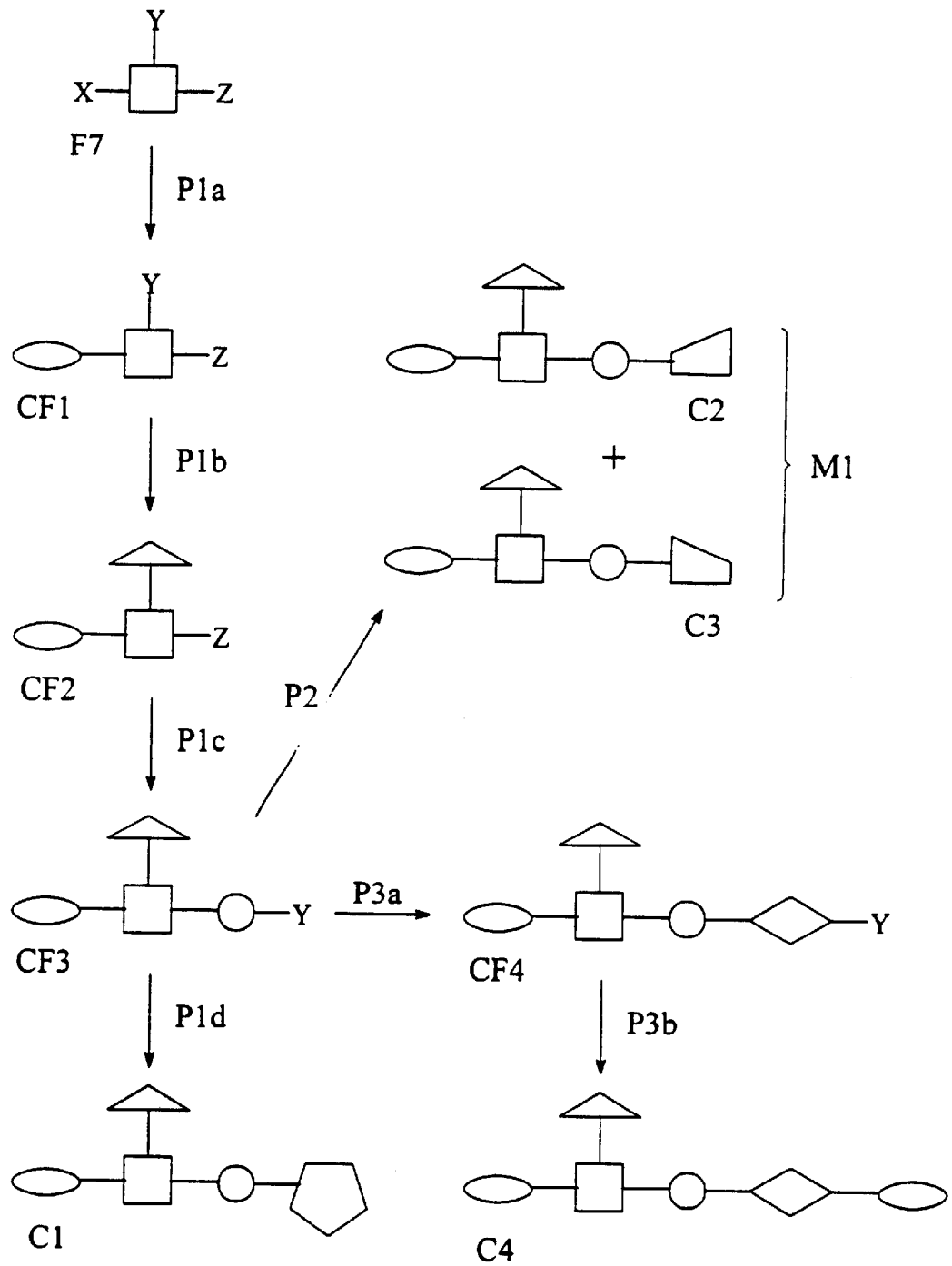
FIG. 11 shows the generation of individual compounds, compounds C1 and C4, and a mixture, mixture M1.
Figure 12:
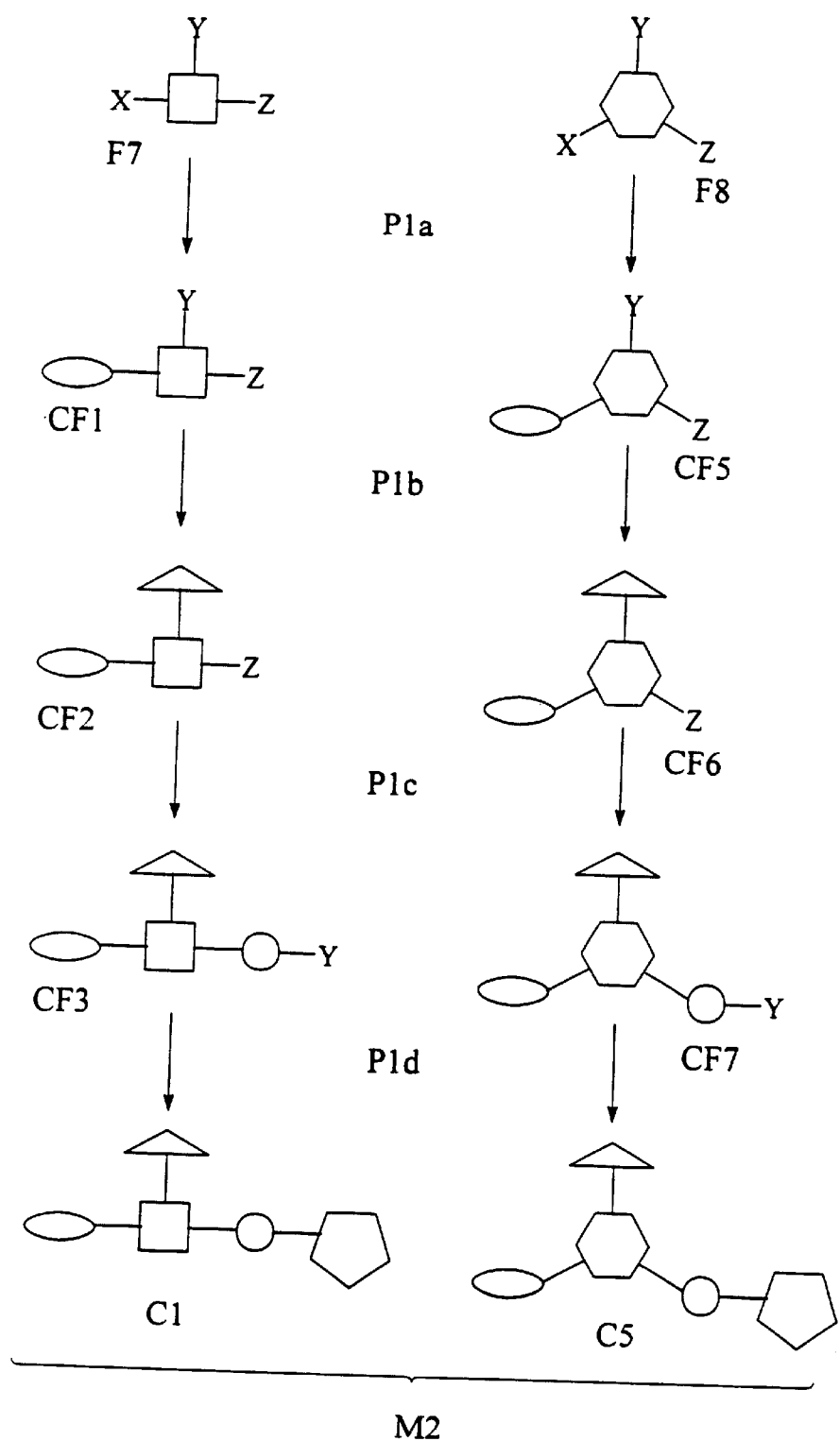
FIG. 12 shows the generation of further mixture, mixture M2.

The methods of the present invention may be used to generate single compounds or mixtures of compounds. A mixture comprises two or more compounds and may involve the use of two or more reagents (thus introduction of two or more fragments) at the outset of library generation, introduction of a mixture of reagents (thus a mixture of fragments) at a subsequent stage of library generation, or a combination of both such techniques. FIGS. 11 and 12 illustrate this aspect of the present invention.

As shown in FIG. 11, the methods of the present invention may be used to generate single compounds such as C1 and C4, or may also be used to generate a mixture of compounds, M1, comprising compounds C2 and C3. Library generation commences with selecting fragment F7 (with three attachment sites), in the first round (i.e. round n). In the second synthesis round (i.e. round n+1), F7 is combined with fragment F2, constituting synthetic pathway P1$a$, and resulting in the formation of complex fragment CF1. F7 possesses three attachment sites (i.e. X, Y and Z). Thus round n+1 will not be complete until each of X, Y and Z have been used, if desired, to attach other fragments to. Stepping around each of X, Y and Z, and attaching fragments to these sites, occurs in that sequential order. Once sites X, Y and Z of the fragment selected in the first synthesis round (i.e. round n) have been exhausted, stepping around the attachment sites present in the next added fragment constitutes the next synthesis round (i.e. the third synthesis round, or round n+2). Here again, when all desired attachment sites on this fragment have been used, that particular synthesis round is complete. This attachment iteration around the desired and available attachment sites of the fragments added continues until the desired compounds have been generated.

As shown in FIG. 11, CF1 is next subjected to synthetic pathway P1$b$ wherein fragment F1 is introduced into CF1, thereby forming complex fragment CF2. CF2 is then subjected to synthetic pathway P1$c$ wherein fragment F5 is added to CF2, leading to the formation of complex fragment CF3. This completes synthesis round n+1 (i.e. the second round of fragment introduction, or synthesis, to build the compound). As fragment F5 has two attachment sites, CF3 has an available attachment site (i.e. site Y). Introduction of fragments to this site (Y site) constitutes synthesis round n+2 (i.e. the third round) because all the desired attachment sites on the previously added fragment have been exhausted. Next, CF3 is subjected to synthetic pathway P2 wherein fragment F4 is introduced into CF3 at attachment site Y. As F4 is a mixture of two components, a mixture (M1) of two compounds, C2 and C3, is generated.

A single compound, however, may also be generated using the present scheme of fragment introduction. Thus, compound C1 can be generated by subjecting CF3 to synthetic pathway P1$d$ wherein CF3 is combined with fragment F3, which attaches to site Y in CF3. The introduction of fragment F3 into CF3 constitutes the third synthesis round (i.e. round n+2), leading to the generation of C1.

Alternately, CF3 can be subjected to synthetic pathway P3$a$ wherein fragment F6 is introduced into CF3 to form CF4. This represents the third synthesis round (i.e. round n+2). CF4 has one more available attachment site (i.e. site Y) to which fragment F2 may be attached via synthetic pathway P3$b$. This leads to the generation of compound C4 which is a compound of increased complexity because of the number of attachment sites on the chosen fragments and synthetic pathways employed. The addition of fragment F6 to CF4 constitutes the third synthesis round (i.e. round n+2). Addition of fragment F2 to CF4 represents the fourth synthesis round, or round n+3, because P3$b$ involves addition of a fragment (fragment F2) onto a site (i.e. site Y in CF4) which has been generated by adding fragment F6 to CF3, thus exhausting the available attachment sites on the previously added fragment in CF4 (i.e. fragment F5). That is, the addition of fragment F6 completed round n+2 (or the third synthesis round) because F6 attached to the last available attachment site on CF3 (i.e. site Y in CF3).

For the reactions effected at path P1$c$ in FIG. 11, a single fragment (F5) can be added to CF2 via use of either reagents R6 or R7 (as thus via the transformations associated with R6 and R7). While these additions are represented as two unique transformations for the purpose of tracking in the database on the invention, these additions in effect perform the same chemical conversion. Thus, the simultaneous tracking of compounds generated according to the methods of the invention is useful not only in working with virtual libraries of compounds, but also provide the user with a choice of synthetic pathways along which the compounds can be actually synthesized. This tracking aspect of the present invention is, therefore, a novel and unique way to account for the fragments being introduced, the related transformations (or reactions) associated with the fragments, and the alternate transformations that lead to the introduction of a common fragment into the desired compounds. The present invention allows not only the tracking of individual compounds that are generated by the use of multiple reagents, but also allows for the simultaneous tracking of multiple compounds that are generated via multiple transformations. While the methods described herein represent the tracking aspects of the invention in terms of symbolic representations or tables, it is recognized by the art-skilled that a variety of computer algorithmic codes and techniques may be employed for the individual or simultaneous tracking aspects described above.

The present invention further provides methods for the one-pot generation of mixtures of compounds by commencing the library generation using different starting fragments in a one-pot fashion. One-pot generation or synthesis of compounds refers to the formation of multiple compounds in a single reaction vessel (i.e. one pot). This is possible if compatible chemistries are selected. Examples of such single vessels include but are not limited to multiple well plates, e.g. a 96-well plate, reactions flasks, e.g. a 25 mL flask, or even an industrial reactor. The reactions, or transformations, are performed in one vessel regardless of the size of the reaction vessel. The concept of one-pot synthesis is irrelevant to the generation of virtual libraries of compounds as these virtual libraries are merely generated in silico. The concept of one-pot synthesis becomes relevant, however, when the actual synthesis of libraries of compounds is to be undertaken. Thus the compounds can be tracked separately for compound building in order to generate distinct chemical structures, however, they can be group together for synthesis allowing them to be made in the same "pot." An example of a one-pot synthesis was shown in FIG. 11 with the addition of the complex reagent R5 to form mixture M1. A further one-pot synthesis is shown in FIG. 12, where a further mixture of compounds is generated. Mixture M2 comprising compounds C1 and C5 can be generated by starting with fragments F7 and F8 in the first synthesis round (i.e. round n). Each of these fragments have three attachment sites onto which other fragments can be introduced. As a result, subjecting the two fragments to synthetic pathway P1a wherein F7 and F8 are combined with fragment F5 at site X, results in the one-pot formation of complex fragments CF1 and CF5. CF1 and CF5 are next subjected to synthetic pathway P1b wherein fragment F1 is introduced into CF1 and CF5 at site Y, thereby forming complex fragments CF2 and CF6. CF2 and CF6 are next subjected to synthetic pathway P1c wherein fragment F5 is introduced into these complex fragments at site Z, forming CF3 and CF7. This completes the second synthetic round (i.e. round n+1). As fragment F5 contains two attachment sites, after introduction into CF3 and CF7, there is still available an attachment site (i.e. site Y) for further introduction of another fragment Thus CF3 and CF7 are converted to a mixture (M2) of compounds C1 and C5 via synthetic pathway P1d wherein CF3 and CF7 are combined with fragment F3 which attaches to the Y site on fragment F5 in CF3 and CF7. The introduction of fragment F3 at site Y in CF3 and CF7 represents the third synthetic round (i.e. round n+2).

Figure 13:
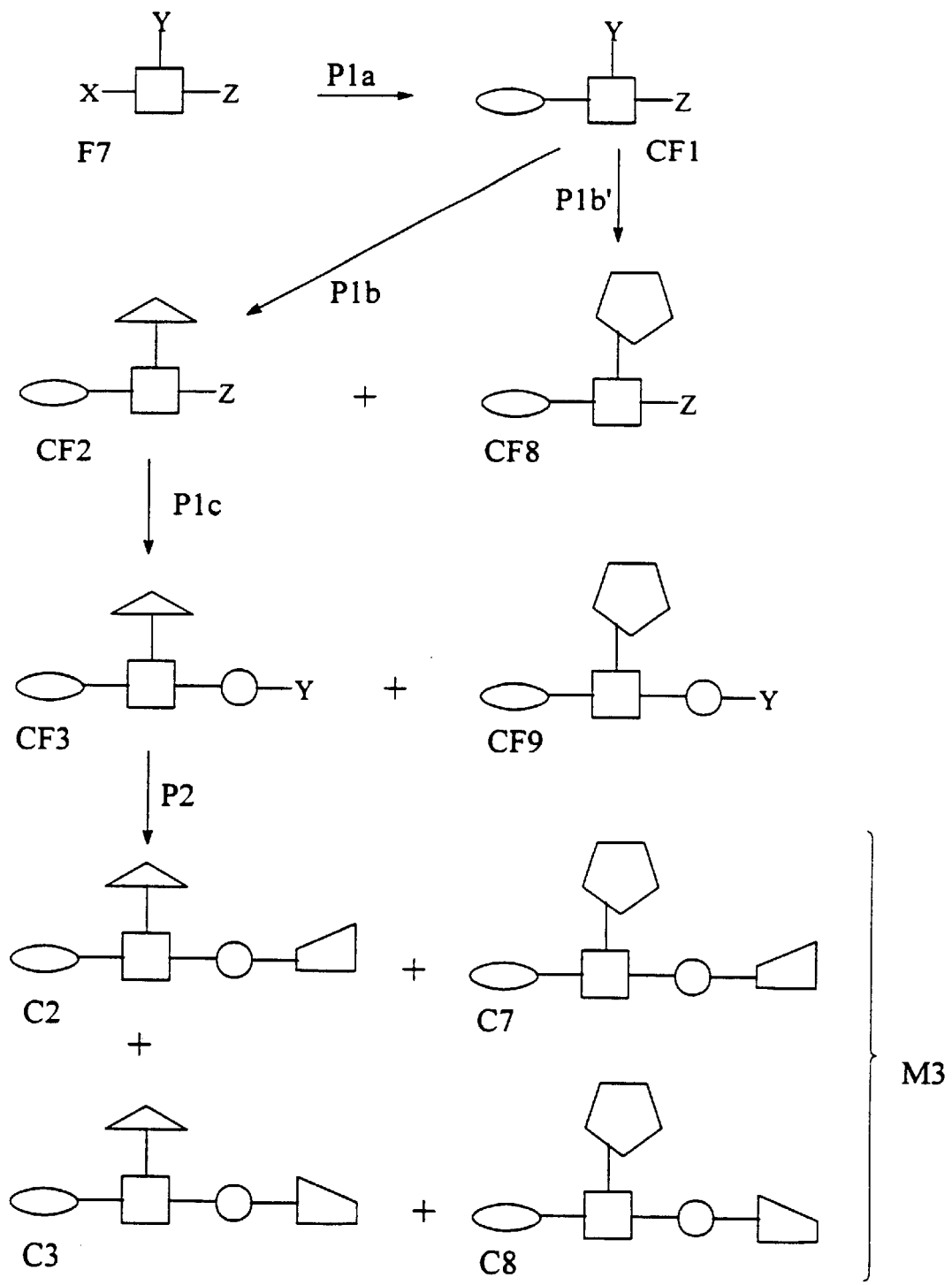
FIG. 13 shows the generation of an additional mixture, mixture M3.

Yet another symbolic example of the one-pot generation of mixtures of compounds, in accordance with the present invention, is shown in FIG. 13. In silico generation of compounds commences with the selection of fragment F7, which has three sites of attachment (X, Y, and Z). This represents the first synthesis round (i.e. round n). Next, F7 is subjected to synthetic pathway P1a wherein F7 is combined with fragment F2. F2 attaches to site X on fragment F7, forming complex fragment CF1. At this stage, CF1 is subjected to two synthetic pathways, P1b and P1b'. P1b employs fragment F1 which is introduced onto site Y on CF1, thereby forming complex fragment CF2, while P1b' employs fragment F3 which is introduced onto site Y on CF1, thereby forming complex fragment CF8. Thus a mixture of complex fragments (CF2 and CF8) are formed. Both fragments, F1 and F3 can be introduced together (such as from a single reagent bottle when actual synthesis is being undertaken) for the one-pot generation of compounds if the chemistries associated with introduction of these fragments into the compounds are compatible. If not, these fragments can be introduced separately. Next, CF2 and CF8 are subjected to synthetic pathway P1c wherein both complex fragments are combined with fragment F5 which attaches to site Z on CF2 and CF8, thereby forming complex fragments CF3 and CF9. The formation of CF3 and CF9 completes the second synthesis round (i.e. round n+1). As fragment F5 has two sites of attachment, site Y is still available for attachment to another fragment. Therefore, CF3 is subjected to synthetic pathway P3 wherein CF3 is combined with fragment F4. Introduction of F4 represents the third synthesis round (i.e. round n+2). F4 is a mixture of fragments (and introduced by adding a mixture of reagents), as shown in FIG. 9. As a result, synthetic pathway P2 leads to the generation of compounds C2 and C3. Simultaneously, CF9 combines with fragment F4, via synthetic pathway P2', leading to the generation of compounds C7 and C8. Thus mixture M3 is formed comprising compounds C2, C3, C7 and C8.

Figure 14B:
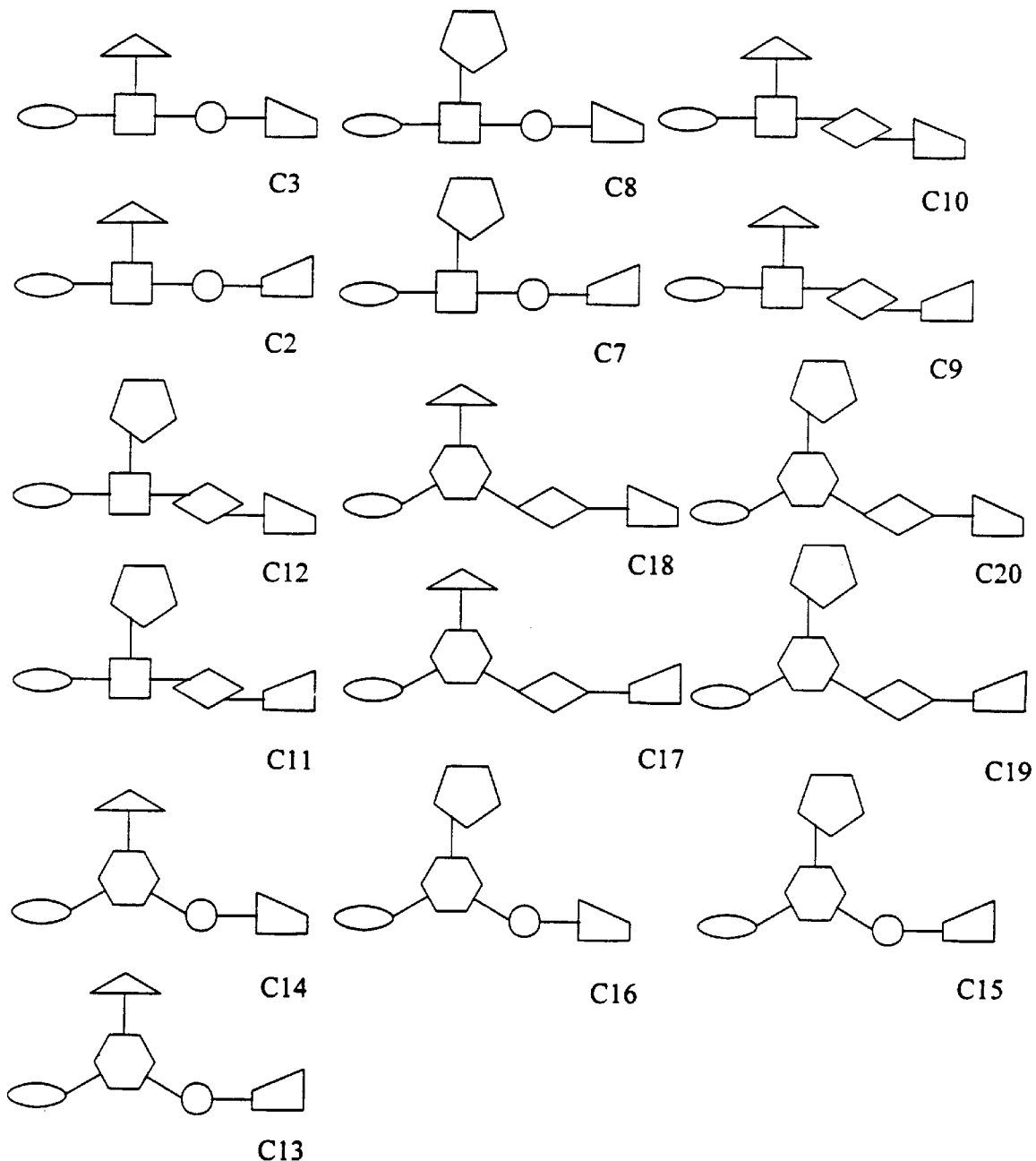

The present invention also provides methods for the generation of increasingly complex mixtures of compounds. An example is shown in FIGS. 14a and 14b where mixture M4 is generated and comprises sixteen compounds. The compounds in mixture M4 can be generated by starting with fragments F7 and F8 in the first synthesis round (i.e. round n). These fragments can then be combined with fragment F2, which is introduced at site X in each of F7 and F8, forming complex fragment CF1 and CF5. Following this, a mixture of fragments F1 and F3 are introduced into CF1 and CF5 at site Y of these complex fragments, leading to the formation of four complex fragments, CF2, CF6, CF8 and CF11. These complex fragments are next combined with a mixture of fragments F5 and F6. Both F5 and F6 have two attachment sites such that site X on F5 and F6 attaches to site Z on CF2, CF6, CF8 and CF11 forming a mixture of eight complex fragments, CF3, CF7, CF9, CF12, CF13, CF14, CF15 and CF16. This completes the second synthesis round (i.e. round n+1). As fragments F5 and F6 have two attachment sites, X and Y, the abovementioned eight complex fragments have one more available attachment site (i.e. site Y) onto which another fragment may be introduced. Attachment of a fragment to site Y on these eight complex fragments represents the third synthesis round (i.e. round n+2). Next, fragment F4 is introduced into CF3, CF7, CF9, CF12, CF13, CF14, CF15 and CF16. As fragment F4 is a mixture of two constituent fragments, sixteen compounds are generated: C2, C3, C7, C8, C9, C10, C11, C12, C13, C14, C15, C16, C17, C18, C19 and C20. Thus it can be seen that by using multiple fragments in a one-pot fashion and combining with mixtures of fragments, mixtures of compounds of increasing complexity can be generated. The example in FIGS. 14a and 14b shows sixteen unique compounds being generated as mixture M4 when the library is generated by starting with two fragments. It is recognized by the art-skilled that if the library generation is commenced with more than two fragments or multiple fragments are added to the same precursor fragment, even more complex mixtures of compounds can be generated.

The present invention also provides methods for keeping track of fragment addition in the various synthesis rounds. This system of accounting is accomplished by tabulation of the synthesis rounds which are correlated with addition of fragments. While for the purposes of illustration of the invention, a tabulation method of tracking fragment addition is described herein, it will be recognized by the art-skilled that other algorithms, algorithmic codes, computer readable mediums and various software coding techniques know to those skilled in the computer arts may be used for such tracking. The tables tracking fragment addition can be used to produce structural representations of compounds and create virtual libraries where actual synthesis of the compounds is not desired. Tables tracking transformations, however, can be used to synthesize compounds by selecting the appropriate transformations, and in the case of multiple transformations, selecting the preferable transformations to introduce the required fragment into the compounds being synthesized.

FIG. 15 is descriptive of compound C1 in terms of the fragments added in each synthesis round. The first synthesis round (i.e. round n) commences with the selection of fragment F7. This is followed by the sequential addition of fragments F2, F1 and F5 in the second synthesis round (i.e. round n+1). Finally, compound C1 is generated by the addition of fragment F3 in the third synthesis round (i.e. round n+2). The compounds thus generated can be stored as a 2-dimensional virtual library, or may be converted to a 3-dimensional virtual library that can be used for in silico docking to desired target molecules.

For the generation of virtual libraries of compounds and for docking the library members onto target molecules, it suffices to add compounds to the relational database in terms of its fragments to track the addition of fragments in the various synthetic rounds. However, when the actual synthesis of desired compounds of a library is to be undertaken, it becomes necessary to specify the actual synthetic steps, reagents, solvents, concentrations, auxiliary compounds needed and other various synthetic factors in order to effect such an actual synthesis of real chemical compounds. Such synthetic steps, reagents, solvents, concentrations and auxiliary compounds are, in fact, incorporated in to the above described transformations. Thus by employing the concept of transformations, the present invention provides methods to track the compounds generated not only in terms of the fragments added but as well as the synthetic parameters necessary for each synthesis round.

FIG. 15 also shows the generation of compound C1 in terms of the various transformations employed in the synthesis rounds. Four synthesis pathways lead to the synthesis of compound C1 because of the availability of multiple transformations that can introduce the same fragment into the compound being synthesized. Thus, as seen in FIG. 15, selection of fragment F7 constitutes transformation T9 in the first synthesis round (i.e. round n). This is followed by the addition of fragment F2 which is achieved by employing transformation T2. Next, fragment F1 is added via transformation T1. Fragment F5, however, may be added by employing either reagent R6 via transformation T6 along synthesis paths 1 and 3, or reagent R7 via transformation T7 along synthesis paths 2 and 4. Similarly, the final fragment F3 can be added by using either reagent R3 via transformation T3 along synthesis paths 1 and 2, or reagent R4 via transformation T4 along synthesis paths 3 and 4. Thus FIG. 15 shows that compound C1 can be actually synthesized via one of four different synthetic schemes which can be tracked or tabulated and accounted for using the methods of the present invention. Each of the four tables is completely descriptive of each of the four synthetic pathways for the preparation of C1. Thus, a user of the present invention has available all the alternate pathways of performing the same reaction (i.e. introducing the same fragment), and can select the preferable or most appropriate synthetic route to preparing the desired compounds.

FIG. 16 shows a similar transformation tracking table for compounds C2 and C3 in mixture M1. Synthesis of compounds C2 and C3 commences with selection of fragment F7 which represents transformation T9 (step 1 in FIG. 16) in the first synthesis round (i.e. round n). Next, F7 is combined with fragment F2 via transformation T2 in the second synthesis round (i.e. round n+1) (step 2). In the same round, fragment F1, via transformation T1, and fragment F5, via transformation 7 are added sequentially (steps 3 and 4). Finally, fragment F4 is added in the third synthesis round (i.e. round n+2). As F4 is a mixture of two constituent fragments (because of two constituent reagents), the table is duplicated at this stage (step 5) to account for the different synthetic ways in which transformation T5 may be accomplished (i.e. T5$^1$ and T5$^2$). Step 5 represents compounds C2 and C3. Thus it can be seen that, in accordance with the present invention, whenever there is more than one reagents associated with a particular transformation, the table is duplicated as many times as there are such reagents.

FIG. 17 shows a transformation tracking table for compounds C1 and C5 in mixture M3. As the synthesis commences with two fragments, F7 and F8, tracking begins with two parallel tables (step 1 in FIG. 17). In the first synthesis round (i.e. round n), F7 is selected via transformation T9, while F8 is selected via transformation T10. The second synthesis round (i.e. round n+1) commences at step 2 with the introduction of fragment F2 via transformation T2. In step 3, transformation T1 introduces fragment F1 into the compound. In step 4, transformation T7 introduces fragment F5. This completes the second synthesis round (i.e. round n+1). Finally, in the third synthesis round (i.e. round n+2), transformation T4 is used to introduce fragment F3 (at step 5) producing mixture M2 comprising compounds C1 and C5. In this example, the tables are duplicated early in the synthetic scheme because of the use of a mixture of fragments F7 and F8 at the outset.

The transformation tracking table for compounds C2, C3, C7 and C8 of mixture M3 are shown in FIG. 18. The synthesis of these compounds commences with the first synthesis round (i.e. round n) in which fragment F7 is selected. This represents transformation T9 (shown in step 1 in FIG. 18). Step 2 in FIG. 18 depicts the second synthesis round (i.e. round n+1) and involves the addition of fragment F2 via transformation T2. While steps 1 and 2 involve single transformations each, step 3 involves two different transformations because two different fragments are being introduced into the compounds through the use of two different reagents. Therefore, at step 3 the table is twice duplicated because two different reagents are being employed to introduce two different fragments via two different transformations. In step 3, transformation T1 is used to introduce fragment F1 while transformation T3 is used to introduce fragment F3. The second synthesis round (i.e. round n+1) is completed at step 4 with transformation T7 which introduces fragment F5. In the final synthesis round (i.e. the third round or round n+2), transformation T5 is used to introduce fragment F4. As F4 is a mixture of two constituent fragments, each table at step 5 is twice duplicated for transformations T5$^1$ and T5$^2$ which represent each of the constituent fragments of F4.

These figures represent merely one manner in which the various fragments, reagents and transformations may be tracked during the generation or synthesis of single compounds or mixtures of compounds. It will, however, be recognized by the art-skilled that various other algorithm schemes may be employed to track and account for the fragments being introduced via transformations when compounds are being generated in silico.

The library members or compounds generated according to the methods of the present invention can be converted into three-dimensional representations using commercially available software. Next, the compounds, in their three-dimensional structures can be docked onto identified targets, also represented as three-dimensional structures.

Docking of these library members (or ligands) entails the in silico binding of the members to desired target molecules. A variety of theoretical and computational methods are known in the literature to study and optimize the interactions of small molecules with biological targets such as proteins and nucleic acids. These structure-based drug design tools have been very useful in modeling the interactions of proteins with small molecule ligands and in optimizing these interactions. Typically this type of study was performed when the structure of the protein receptor was known by querying individual small molecules, one at a time, against this receptor. Usually these small molecules had either been co-crystallized with the receptor, were related to other molecules that had been co-crystallized or were molecules for which some body of knowledge existed concerning their interactions with the receptor. A significant advance in this area was the development of a software program called DOCK that allows structure-based database searches to find and identify the interactions of known molecules to a receptor of interest (Kuntz et al., *Acc. Chem. Res.,* 1994, 27, 117; Gschwend and Kuntz, *J Compt.-Aided Mol. Des.,* 1996, 10, 123). DOCK allows the screening of molecules, whose 3D structures have been generated in silico, but for which no prior knowledge of interactions with the receptor is available. DOCK, therefore, provides a tool to assist in discovering new ligands to a receptor of interest DOCK can thus be used for docking the compounds prepared according to the methods of the present invention to desired target molecules.

The DOCK program has been applied to protein targets and the identification of ligands that bind to them. The DOCK software program consists of several modules, including SPHGEN (Kuntz et al., *J. Mol. Biol.,* 1982, 161,269) and CHEMGRID (Meng et al., *J. Comput. Chem.,* 1992, 13, 505). SPHGEN generates clusters of overlapping spheres that describe the solvent-accessible surface of the binding pocket within the target receptor. Each cluster represents a possible binding site for small molecules. CHEMGRID precalculates and stores in a grid file the information necessary for force field scoring of the interactions between binding molecule and target. The scoring function approximates molecular mechanics interaction energies and consists of van der Waals and electrostatic components. DOCK uses the selected cluster of spheres to orient ligands molecules in the targeted site on the receptor. Each molecule within a previously generated 3D database is tested in thousands of orientations within the site, and each orientation is evaluated by the scoring function. Only that orientation with the best score for each compound so screened is stored in the output file. Finally, all compounds of the database are ranked in order of their scores and a collection of the best candidates may then be screened experimentally.

Using DOCK, ligands have been identified for certain protein targets. Recent efforts in this area have resulted in reports of the use of DOCK to identify and design small molecule ligands that exhibit binding specificity for nucleic acids such as RNA double helices. While RNA plays a significant role in many diseases such as AIDS, viral and bacterial infections, few studies have been made on small molecules capable of specific RNA binding. Compounds possessing specificity for the RNA double helix, based on the unique geometry of its deep major groove, were identified using the DOCK methodology (Chen et al., *Biochemistry,* 1997,36, 11402; Kuntz et al., *Acc. Chem. Res.,* 1994, 27, 117). Using a recent X-ray structure for r(UAAGGAGGUGAU).r(AUCACCUCCUUA) as the model structure for the A-form RNA duplex, DOCK identified several aminoglycosides as candidate ligands, characterized by shape complementarity to the RNA groove. Binding experiments then revealed that one of these aminoglycosides not only bound preferentially to RNA over B-form DNA but also that the ligand binds in the targeted RNA major groove. Recently, the application of DOCK to the problem of ligand recognition in DNA quadruplexes has also been reported (Chen et al., *Proc. Natl. Acad. Sci.,* 1996, 93, 2635).

As yet there has been no report of the evaluation of virtual libraries against RNA targets. Certain reports of the generation of virtual libraries are available from the standpoint of library design, generation, and screening against protein targets. Likewise, some efforts in the area of generating RNA models have been reported in the literature. However, there are no reports on the use of structure-based design approaches to query virtual libraries against three-dimensional models of RNA structure so as to identify ligands, such as small molecules, oligonucleotides or other nucleic acids, that bind to such targets. The present invention provides a solution to this problem by allowing the building of three-dimensional models of RNA structure, the building of virtual libraries of ligands, including small molecules, polymeric compounds, oligonucleotides and other nucleic acids, screening of such virtual libraries against RNA targets in silico, scoring and identifying the best potential binders from such libraries, and finally, synthesizing such molecules in a combinatorial fashion and testing them experimentally to identify new ligands for such targets.

The methods of the present invention aid in the drug discovery process by allowing the identification of those library members which bind with high affinity to the target molecules and, therefore, represent molecules that may be actually synthesized and developed as lead drug candidates.

What is claimed is:

1. A method of generating a virtual library of compounds in silico comprising:

selecting in silico a group of related fragments, each of said fragments constituting a part of said compounds, each of said related fragments being associated with at least one reagent that can be used to introduce said related fragment into said compound each of said related fragments having at least one attachment site;

selecting in silico at least one further fragment having at least one attachment site, said further fragment being associated with at least one reagent that can be used to introduce said further fragment into said compound; and linking in silico said further fragment to said related fragments by connecting at least one attachment site of said further fragment to at least one attachment site of said related fragments to generate said virtual library of compounds.

2. A method of generating a virtual library of compounds in silico comprising:

selecting in silico a first fragment, said first fragment constituting a part of said compounds and having at least one attachment site, said first fragment being associated with at least one reagent that can be used to introduce said first fragment into said compound;

selecting in silico a group of related fragments, each of said group of related fragments having at least one attachment site, each of said related fragments being associated with at least one reagent that can be used to introduce said related fragment into said compound; and linking in silico each of said group of related fragments to said first fragment by connecting at least one attachment site of each of said group of related fragments to at least one attachment site of said first fragment to generate said virtual library of compounds.

3. A method of generating a virtual library of compounds in silico comprising:

selecting in silico a first group of related fragments, each of said first group of related fragments constituting apart of said compounds and having at least one attachment site each of said related fragments being associated with at least one reagent that can be used to introduce said related fragment into said compound;

selecting in silico a further group of fragments, each of said further group of fragments having at least one attachment site, each of said further group of fragments being associated with at least one reagent that can be used to introduce said fragment into a compound; and linking in silico each of said first group of related fragments to each of said further group of fragments by connecting at least one attachment site of each of said first group of related fragments to at least one attachment site of each of said further group of fragments to generate said virtual library of compounds.

4. A method of generating a virtual library of compounds in silico comprising:

dissecting said compounds into fragments;

representing each of said fragments in silico as a transformation wherein each transformation is a one to one link between a fragment and a reagent used to introduce said fragment into one of said compounds;

selecting in silico a first group of said fragments, each of said first group of fragments constituting a part of said compounds, each of said first group fragments having at least one attachment site;

selecting in silico at least one further fragment having at least one attachment site; and linking in silico said further fragment to said first group of fragments by connecting at least one attachment site of said further fragment to at least one attachment site of said members of said first group of fragments to generate said virtual library of compounds.

5. A method of generating a virtual library of compounds in silico comprising:

dissecting said compounds into fragments;

representing each of said fragments in silico as a transformation wherein each transformation is a one to one link between a fragment and a reagent used to introduce said fragment into one of said compounds;

selecting in silico a fragment, said first fragment constituting a part of said compounds, said first fragment having at least one attachment site;

selecting in silico at group of further fragments each having at least one attachment site; and linking in silico said group of further fragments to said first fragment by connecting at least one attachment site of said group of further fragments to at least one attachment site of first fragment to generate said virtual library of compounds.

6. A method of generating a virtual library of compounds in silico comprising:

dissecting said compounds into fragments;

representing each of said fragments in silico as a transformation wherein each transformation is a one to one link between a fragment and a reagent used to introduce said fragment into one of said compounds;

selecting in silico a first group of said fragments, each of said first group of fragments constituting a part of said compounds, each of said first group fragments having at least one attachment site;

selecting in silico at group of further fragments each having at least one attachment site; and linking in silico at least some of the members of said group of further fragments to least some of members of said first group of fragments by connecting at least one attachment site of the members of said further fragments to at least one attachment site of said members of said first group of fragments to generate said virtual library of compounds.

7. A method of generating a database comprising information about the member compounds of a virtual library of compounds comprising:

selecting each of said compounds for said virtual library and, for each, dissecting each of said compounds into fragments;

linking together the fragments of each of the compounds;

tracking the sequence of linkage for each compound;

grouping two or more compounds of said library together to form a mixture; and linking together the tracked information of each of the members of said mixture; and storing said tracked information thereby generating a database.

8. A method of generating a database comprising information about the member compounds of a virtual library of compounds comprising:

selecting each of said compounds for said virtual library and, for each, dissecting each of said compounds into fragments;

linking together the fragments of each of the compounds;

tracking the sequence of linkage for each compound;

grouping two or more compounds of said library together to form a mixture;

grouping a further two or more compounds of said library together to form a further mixture;

linking together the tracked information of each of the members of said mixture;

linking together the tracked information of each of the members of said further mixture; and storing said tracked information thereby generating a database.

9. A method of generating a database comprising information about member compounds in a virtual library of compounds comprising:

selecting each of said compounds for said virtual library and, for each, dissecting said compounds into fragments;

representing each of said fragments as a transformation wherein each transformation is a one to one link between a fragment and a reagent used to introduce said fragment into one of said compounds;

linking together the transformations of each of the compounds;

tracking the sequence of linkage for each compound; and storing said transformation information thereby generating a database.

10. The method of claim 9 further including:

grouping two or more compounds of said library together to form a mixture; and linking together the tracked information of each of the members of said mixture.

11. The method of claim 9 further including:

grouping two or more compounds of said library together to form a mixture;

grouping a further two or more compounds of said library together to form a further mixture;

linking together the tracked information of each of the members of said mixture; and linking together the tracked information of each of the members of said further mixture.

12. The method of claim 9 further including:

defining each said transformation to further include information related to the synthesis of its fragment from its reagent.

13. A method of generating a database comprising information about the member compounds of a virtual library of compounds comprising:

selecting each of said compounds for said virtual library and, for each, dissecting each of said compounds into fragments;

grouping two or more compounds of said library together to form a mixture;

linking together the fragments of each of the compounds;

tracking the sequence of linkage of the members of said mixture; and storing said tracked information thereby generating a database.

14. A method of generating a database comprising information about the member compounds of a virtual library of compounds comprising:

selecting each of said compounds for said virtual library and, for each, dissecting each of said compounds into fragments;

grouping said compounds of said library into mixtures where each mixture includes two or more member compounds of said library;

linking together the fragments of each of the compounds;

tracking the sequence of linkage of the members of each said mixture; and storing said tracked information thereby generating a database.

15. A method of generating a database comprising information about the member compounds of a virtual library of compounds comprising:

selecting each of said compounds for said virtual library and, for each, dissecting each of said compounds into fragments;

representing each of said fragments as a transformation wherein each transformation is a one to one link between a fragment and a reagent used to introduce said fragment into one of said compounds;

grouping two or more compounds of said library together to form a mixture;

linking together the transformation for each of the compounds;

tracking the sequence of linkage of the members of said mixture; and storing said tracked information thereby generating a database.

16. The method of claim 15 further including:

defining each said transformation to further include information related to the synthesis of its fragment from its reagent.

17. A method of generating a database comprising information about the member compounds of a virtual library of compounds comprising:

selecting each of said compounds for said virtual library and, for each, dissecting each of said compounds into fragments;

representing each of said fragments as a transformation wherein each transformation is a one to one link between a fragment and a reagent used to introduce said fragment into one of said compounds;

grouping said compounds of said library into mixtures where each mixture includes two or more member compounds of said library;

linking together the transformation for each of the compounds;

tracking the sequence of linkage of the members of each said mixture; and storing said tracked information thereby generating a database.

18. The method of claim 17 further including:

defining each said transformation to further include information related to the synthesis of its fragment from its reagent.

\* \* \* \* \*

UNITED STATES PATENT AND TRADEMARK OFFICE
CERTIFICATE OF CORRECTION

PATENT NO. : 6,253,168 B1
DATED : June 26, 2001
INVENTOR(S) : Griffey et al.

It is certified that error appears in the above-identified patent and that said Letters Patent is hereby corrected as shown below:

<u>Title page,</u>
OTHER PUBLICATIONS, please delete "Waters et al." and insert therefor -- Walters et al --;

<u>Column 2,</u>
Line 56, please insert -- into the -- after the word "fragment";

<u>Column 13,</u>
Line 51, please delete "7" and insert therefor -- T7 --;

<u>Column 15,</u>
Line 8, please insert -- . -- after the word "interest";

<u>Column 16, claim 3,</u>
Line 59, please delete "apart" and insert therefor -- a part --;

Signed and Sealed this

Fifth Day of March, 2002

*Attest:*

*Attesting Officer*

JAMES E. ROGAN
*Director of the United States Patent and Trademark Office*